US006835392B2

(12) United States Patent
Hsu et al.

(10) Patent No.: US 6,835,392 B2
(45) Date of Patent: Dec. 28, 2004

(54) DUAL ENHANCER COMPOSITION FOR TOPICAL AND TRANSDERMAL DRUG DELIVERY

(75) Inventors: Tsung-Min Hsu, San Diego, CA (US); Eric C. Jacobson, San Diego, CA (US); Rose C. LoBello, San Diego, CA (US); Eric C. Luo, Plano, TX (US)

(73) Assignee: Dermatrends, Inc., San Diego, CA (US)

( * ) Notice: Subject to any disclaimer, the term of this patent is extended or adjusted under 35 U.S.C. 154(b) by 0 days.

(21) Appl. No.: 10/389,143

(22) Filed: Mar. 13, 2003

(65) Prior Publication Data

US 2003/0161870 A1 Aug. 28, 2003

Related U.S. Application Data

(60) Division of application No. 09/972,008, filed on Oct. 4, 2001, now Pat. No. 6,582,724, which is a continuation-in-part of application No. 09/738,410, filed on Dec. 14, 2000, now Pat. No. 6,586,000, which is a continuation-in-part of application No. 09/569,889, filed on May 11, 2000, now abandoned, which is a continuation-in-part of application No. 09/465,098, filed on Dec. 16, 1999, now abandoned.

(51) Int. Cl.[7] .......................... A61F 13/00; A61L 15/00
(52) U.S. Cl. .................... 424/449; 424/443; 424/445; 424/447; 424/448; 514/946; 514/944
(58) Field of Search ................. 424/449, 443, 424/445, 447, 448; 514/946, 947, 944

(56) References Cited

U.S. PATENT DOCUMENTS

| | | | |
|---|---|---|---|
| 4,704,282 A | 11/1987 | Campbell et al. |
| 4,789,547 A | 12/1988 | Song et al. |
| 4,837,027 A | 6/1989 | Lee et al. |
| 5,071,657 A | 12/1991 | Oloff et al. |
| 5,152,997 A | 10/1992 | Ebert et al. |
| 5,318,960 A | 6/1994 | Toppo |
| 5,432,192 A | 7/1995 | Sawanishi et al. |

(List continued on next page.)

FOREIGN PATENT DOCUMENTS

| | | |
|---|---|---|
| EP | 0276561 | 8/1988 |
| EP | 0316065 | 5/1989 |

(List continued on next page.)

OTHER PUBLICATIONS

U.S. patent application Ser. No. 09/465,098, Luo et al., filed Dec. 16, 1999.

(List continued on next page.)

*Primary Examiner*—Thurman K. Page
*Assistant Examiner*—Isis Ghali
(74) *Attorney, Agent, or Firm*—Reed & Eberle LLP; Dianne E. Reed; Shelley P. Eberle

(57) ABSTRACT

A permeation enhancer composition is provided for increasing the permeability of skin or mucosal tissue to topically or transdermally administered pharmacologically or cosmeceutically active agents. The composition is comprised of a hydroxide-releasing agent and a lipophilic co-enhancer such as a fatty alcohol, a fatty ether, or a fatty acid ester, including fatty acid esters of polyols such as propylene glycol and glycerol. Also provided are pharmaceutical formulations containing a therapeutically effective amount of an active agent in addition to the aforementioned enhancer composition, methods for administering active agents topically or transdermally with enhanced permeation, and drug delivery systems for application to an individual's skin or mucosal tissue, wherein the systems are formulated so as to contain an active agent to be administered and an effective permeation enhancing amount of an enhancer composition of the invention.

48 Claims, 1 Drawing Sheet

U.S. PATENT DOCUMENTS

| | | |
|---|---|---|
| 5,446,070 A | 8/1995 | Mantelle |
| 5,460,820 A | 10/1995 | Ebert et al. |
| 5,462,744 A | 10/1995 | Gupte et al. |
| 5,462,746 A | 10/1995 | Wolter et al. |
| 5,474,783 A | 12/1995 | Miranda et al. |
| 5,498,417 A | 3/1996 | Lhila et al. |
| 5,500,222 A | 3/1996 | Lee et al. |
| 5,527,832 A | 6/1996 | Chi et al. |
| 5,532,278 A | 7/1996 | Aberg et al. |
| 5,534,496 A | 7/1996 | Lee et al. |
| 5,562,917 A | 10/1996 | Durif et al. |
| 5,573,778 A | 11/1996 | Therriault et al. |
| 5,599,554 A | 2/1997 | Majeti |
| 5,614,211 A | 3/1997 | Gale et al. |
| 5,674,895 A | 10/1997 | Guittard et al. |
| 5,807,568 A | 9/1998 | Cody et al. |
| 5,817,332 A | 10/1998 | Urtti et al. |
| 5,830,497 A | 11/1998 | Yamanaka et al. |
| 5,834,513 A | 11/1998 | Ptchelintsev et al. |
| 5,847,003 A | 12/1998 | Ptchelintsev et al. |
| 5,879,690 A | 3/1999 | Perricone |
| 5,939,094 A | 8/1999 | Durif et al. |
| 5,962,018 A | 10/1999 | Curtis et al. |
| 5,985,317 A | 11/1999 | Venkateshwaran et al. |
| 5,985,860 A | 11/1999 | Toppo |
| 5,989,586 A | 11/1999 | Hsu et al. |
| 5,990,113 A | 11/1999 | Yamazaki et al. |
| 5,990,179 A | 11/1999 | Gyory et al. |
| 5,993,851 A | 11/1999 | Foldvari |
| 5,994,372 A | 11/1999 | Yaksh |
| 6,004,577 A | 12/1999 | Murdock |
| 6,019,988 A | 2/2000 | Parab et al. |
| 6,019,997 A | 2/2000 | Scholz et al. |
| 6,123,961 A | 9/2000 | Aberg |
| 6,132,760 A | 10/2000 | Hedenstrom et al. |
| 6,139,866 A | 10/2000 | Chono et al. |
| 6,174,546 B1 | 1/2001 | Therriault et al. |
| 6,204,268 B1 | 3/2001 | Scarborough et al. |
| 6,214,374 B1 | 4/2001 | Schmirler et al. |
| 6,316,011 B1 | 11/2001 | Ron et al. |

FOREIGN PATENT DOCUMENTS

| | | |
|---|---|---|
| EP | 0709088 | 5/1996 |
| EP | 0842662 | 5/1998 |
| FR | 2692145 | 12/1993 |
| JP | 2180835 | 7/1990 |
| JP | 6092843 | 4/1994 |
| KR | 9507098 | 6/1995 |
| WO | WO 94/21271 | 9/1994 |
| WO | WO 99/49844 | 10/1999 |

OTHER PUBLICATIONS

U.S. patent application Ser. No. 09/569,889, Luo et al., filed May 11, 2000.

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

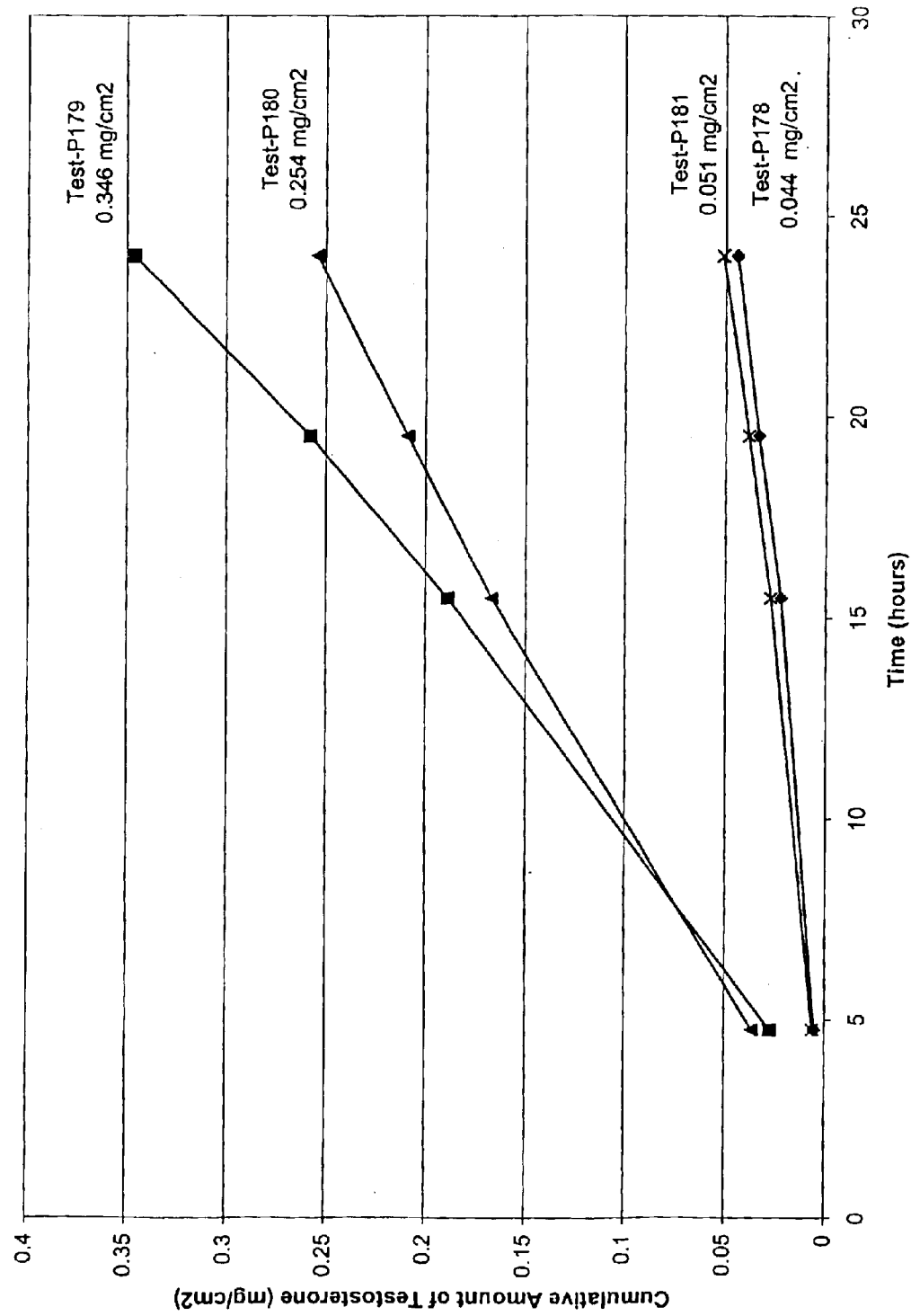
Figure 1. Human Skin Permeation of Testosterone from a Matrix Patch

DUAL ENHANCER COMPOSITION FOR TOPICAL AND TRANSDERMAL DRUG DELIVERY

CROSS-REFERENCE TO RELATED APPLICATIONS

This is a divisional of U.S. patent application Ser. No. 09/972,008, filed Oct. 4, 2001, and now issued as U.S. Pat. No. 6,582,724; which is a continuation-in-part of U.S. patent application Ser. No. 09/738,410, filed Dec. 14, 2000, and now issued as U.S. Pat. No. 6,586,000; which was a continuation-in-part of U.S. patent application Ser. No. 09/569,889, filed May 11, 2000, now abandoned; which was a continuation-in-part of U.S. patent application Ser. No. 09/465,098, filed Dec. 16, 1999, now abandoned; the disclosures of which are incorporated by reference.

TECHNICAL FIELD

This invention relates generally to the topical and transdermal administration of pharmacologically active agents, and more particularly relates to permeation enhancer compositions for enhancing the permeability of skin or mucosal tissue to topically applied pharmacologically active agents.

BACKGROUND ART

Skin is a structurally complex, relatively thick membrane. In order to deliver a drug into and through the skin, i.e., "transdermally," drug molecules must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum that present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

In order to increase the rate at which a drug penetrates through the skin, various approaches have been followed, each of which involves the use of either a chemical penetration enhancer or a physical penetration enhancer. Methods for physically enhancing skin permeation include, for example, electrophoretic techniques such as iontophoresis. The use of ultrasound (or "phonophoresis") as a physical penetration enhancer has also been researched. Chemical enhancers are compounds that are administered along with the drug (or in some cases used to pretreat the skin, prior to drug administration) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Various compounds for enhancing the permeability of skin are known in the art and described in the pertinent texts and literature. Compounds that have been used to enhance skin permeability include: sulfoxides such as dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecyl-cyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. *Percutaneous Penetration Enhancers*, eds. Smith et al. (CRC Press, 1995) provides an excellent overview of the field and further background information on a number of chemical and physical enhancers.

Although many chemical permeation enhancers are known, there is an ongoing need for enhancers that are highly effective in increasing the rate at which a drug permeates the skin, do not result in skin damage, irritation, sensitization, or the like, and can be used to effect transdermal delivery of even high molecular weight drugs such as peptides, proteins, and nucleic acids. Furthermore, it would be a clear advantage commercially if a single enhancer composition could be used to enhance both hydrophilic and hydrophobic drugs. Currently, the enhancers that are used with hydrophilic drugs are not generally effective with hydrophobic drugs, and, conversely, the enhancers that are used with hydrophobic drugs are not generally effective with hydrophilic drugs. It has now been discovered that a combination enhancer, comprised of both a hydrophilic component and a lipophilic component, wherein the hydrophilic component is a hydroxide-releasing agent, is a highly effective permeation enhancer, provide all of the aforementioned advantages relative to known permeation enhancers, and is equally effective with hydrophilic and lipophilic drugs.

SUMMARY OF THE INVENTION

It is thus a primary object of the invention to address the above-described need in the art by providing a novel permeation enhancer composition for enhancing the rate at which an active agent administered to a patient's body surface permeates into and/or through the body surface.

It is another object of the invention to provide such an enhancer composition, wherein the composition contains a hydroxide-releasing agent and a lipophilic co-enhancer.

It is still another object of the invention to provide such an enhancer composition, wherein the lipophilic co-enhancer comprises a fatty acid ester, a fatty alcohol, a fatty ether, or a derivative and/or combination thereof.

It is yet another object of the invention to provide a pharmaceutical formulation containing a therapeutically effective amount of a pharmacologically active agent and an effective permeation enhancing amount of an enhancer composition of the invention.

It is a further object of the invention to provide a drug delivery system for application to a patient's body surface, containing a therapeutically effective amount of a pharmacologically active agent and an effective permeation-enhancing amount of an enhancer composition of the invention.

It is still a further object of the invention to provide a method for enhancing the flux of an active agent through a body surface, wherein the method involves administering the agent to a localized region of a human patient's body surface in combination with an effective permeation enhancing amount of an enhancer composition of the invention.

It is yet a further object of the invention to provide such a method wherein the active agent is intended for local delivery, and drug administration is topical.

It is an additional object of the invention to provide such a method wherein the active agent is intended for systemic delivery, and drug administration is transdermal.

Additional objects, advantages and novel features of the invention will be set forth in part in the description that follows, and in part will become apparent to those skilled in the art upon examination of the following, or may be learned by practice of the invention.

In one aspect of the invention, then, a permeation enhancer composition is provided that is comprised of a hydroxide-releasing agent and a lipophilic co-enhancer, wherein the weight ratio of the hydroxide-releasing agent to the lipophilic co-enhancer is generally in the range of approximately 1:99 to approximately 99:1, preferably in the range of approximately 1:20 to approximately 20:1, and most preferably in the range of approximately 1:2 to approximately 2:1. The hydroxide-releasing agent is generally selected from the group consisting of inorganic hydroxides, inorganic oxides, metal salts of weak acids, and mixtures thereof, although inorganic hydroxides, i.e., ammonium hydroxide, alkali metal hydroxides, and alkaline earth metal hydroxides, are preferred. The lipophilic co-enhancer has a molecular weight in the range of about 150 to 1000 and an aqueous solubility of less than about 1 wt %. Preferably, the co-enhancer also has a Hildebrand solubility parameter $\sigma$ in the range of about 2.5 to about 12, preferably in the range of about 5 to about 10. Preferred co-enhancers have the molecular structure $(CH_3-L-X)_nR$, in which:

n is 1 or 2;

L is alkylene or alkenylene containing 1 to 3 double bonds and from about 6 to about 22 carbon atoms;

X is selected from the group consisting of —COO—, —CH$_2$O— and —CH$_2$O—(CO)—; and R is selected from the group consisting of H, lower alkyl, and lower alkyl substituted with one or two hydroxyl groups, with the proviso that if R is H, X is necessarily —CH$_2$O—, wherein when n is 2, R contains at least two carbon atoms.

Preferred lipophilic co-enhancers are fatty acid esters, particularly lower alkyl esters of a $C_{10}$–$C_{18}$ fatty acid, and $C_{10}$–$C_{18}$ fatty acid mono- and di-esters of polyols such as propylene glycol and glycerol. Preferably, although not necessarily, the enhancer composition has a pH in the range of approximately 8.0 to approximately 13.0, more preferably in the range of approximately 8.0 to 11.5, and optimally in the range of approximately 8.0 to approximately 11.5.

In another aspect of the invention, a pharmaceutical formulation is provided containing a therapeutically effective amount of a pharmacologically active agent, an effective permeation enhancing amount of a permeation enhancer composition as just described, and a pharmaceutically acceptable carrier suitable for topical or transdermal drug administration. The formulation may be in any form suitable for application to the body surface, and may comprise, for example, a cream, lotion, solution, gel, ointment, paste or the like, and/or may be prepared so as to contain liposomes, micelles, and/or microspheres. The formulation may be directly applied to the body surface or may involve use of a drug delivery device. It is preferred although not essential that water be present in order for the hydroxide-releasing agent to generate hydroxide ions and thus assist in enhancing the flux of the active agent through a patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration.

The amount of the hydroxide-releasing agent in the pharmaceutical formulation is preferably the total of (a) the amount required to neutralize any acidic species in the formulation plus (b) an amount equal to approximately 0.5 wt % to 4.0 wt % of the formulation. When the active agent is an acid addition salt of a basic compound, the amount in (a) is the amount required to neutralize the acid addition salt and any other acidic species in the formulation. When the active agent is an acidic drug in the form of a free acid, the amount in (a) is the amount required to neutralize the acidic drug and any other acidic species in the formulation. With basic drugs present in the formulation as a neutral, free base, and with basic salts of acidic drugs, the amount in (a) is simply the amount necessary to neutralize inactive components that are acidic, since such drugs are not, clearly, susceptible to neutralization with base. Preferably, although not necessarily, the pharmaceutical formulation has a pH in the range of approximately 8.0 to approximately 13.0, more preferably in the range of approximately 8.0 to 11.5, and optimally in the range of approximately 8.0 to approximately 11.5.

In a further aspect of the invention, a drug delivery system is provided for the topical or transdermal administration of a drug using the dual enhancer composition of the invention. The system will generally comprise: at least one drug reservoir containing the drug and the enhancer composition in an amount effective to enhance the flux of the drug through the body surface; a means for maintaining the system in drug and enhancer transmitting relationship to the body surface; and a backing layer that serves as the outer surface of the device during use. The backing layer may be occlusive or nonocclusive, although it is preferably occlusive. The drug reservoir may be comprised of a polymeric adhesive, which may serve as the basal surface of the system during use and thus function as the means for maintaining the system in drug and enhancer transmitting relationship to the body surface. The drug reservoir may also be comprised of a hydrogel, or it may be a sealed pouch within a "patch"—type structure wherein the drug and hydroxide-releasing agent are present in the pouch as a liquid or semi-solid formulation.

In an additional aspect of the invention, a method is provided for increasing the rate at which an active agent permeates through the body surface of a patient. The method involves administering the agent to a predetermined area of the patient's body surface in combination with an effective permeation-enhancing amount of a permeation enhancer composition of the invention. The effective permeation enhancing amount of the enhancer composition is preferably an amount effective to provide a pH at the body surface, i.e., during drug administration, in the range of about 8.0 to 13, preferably about 8.0 to 11.5, most preferably about 8.5 to 11.5. If a skin patch is used, this is the preferred pH at the interface between the basal surface of the patch (i.e., the skin-contacting or mucosa-contacting surface of the patch) and the body surface. The optimal amount (or concentration) of the enhancer composition will, however, depend on the specific hydroxide-releasing agent, i.e., on the strength or weakness of the base, its molecular weight, and other factors as will be appreciated by those of ordinary skill in the art of transdermal drug delivery. This optimal amount may be determined using routine experimentation to ensure that the pH at the body surface is within the aforementioned ranges, i.e., in the range of about 8.0 to 13, preferably about 8.0 to 11.5, most preferably about 8.5 to 11.5. A conventional transdermal drug delivery device or "patch" may be used to administer the active agent, in which case the drug and hydroxide-releasing agent are generally present in a drug reservoir or reservoirs. However, the drug and hydroxide-releasing agent may also be administered to the body surface using a liquid or semisolid formulation. Alternatively, or in addition, the body surface may be pretreated with the enhancer, i.e., prior to transdermal drug administration.

BRIEF DESCRIPTION OF THE DRAWING

FIG. 1 is a graph illustrating the cumulative amount of testosterone permeated through the skin with a dual enhancer composition of the invention, a composition containing only one of the enhancers, and a composition containing no enhancers, as described in detail in the Example.

DETAILED DESCRIPTION OF THE INVENTION

I. Definitions and Overview

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a pharmacologically active agent" refers not only to a single active agent but also to a mixture of two or more active agents, reference to "a hydroxide-releasing agent" includes mixtures of two or more hydroxide-releasing agents, the term "a lipophilic co-enhancer" can refer to two or more lipophilic components in combination, and the like.

In describing and claiming the present invention, the following terminology will be used in accordance with the definitions set out below.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be one that is acted upon chemically in an aqueous environment to generate hydroxide ions (e.g., a metal carbonate).

The terms "active agent," "drug" and "pharmacologically active agent" are used interchangeably herein to refer to a chemical material or compound that induces a desired effect, and include agents that are therapeutically effective, .prophylactically effective, or cosmeceutically effective. Also included are derivatives and analogs of those compounds or classes of compounds specifically mentioned that also induce the desired effect.

By "therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug or pharmacologically active agent to the skin or mucosa, as in, for example, the treatment of various skin disorders. Topical administration, in contrast to transdermal administration, provides a local rather than a systemic effect. Unless otherwise stated or implied, the terms "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which a drug-enhancer formulation is delivered, is intended a defined area of intact unbroken living skin or mucosal tissue. That area will usually be in the range of about 5 cm$^2$ to about 200 cm$^2$, more usually in the range of about 5 cm$^2$ to about 100 cm$^2$, preferably in the range of about 20 cm$^2$ to about 60 cm$^2$. However, it will be appreciated by those skilled in the art of drug delivery that the area of skin or mucosal tissue through which drug is administered may vary significantly, depending on patch configuration, dose, and the like.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example a Franz diffusion apparatus as known in the art and as employed in the Examples herein.

An "effective amount" or "an effective permeation enhancing amount" of a permeation enhancer refers to a nontoxic, nondamaging but sufficient amount of the enhancer composition to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art, which are nontoxic and do not interact with other components of a pharmaceutical formulation or drug delivery system in a deleterious manner.

Accordingly, the invention pertains to an enhancer composition, pharmaceutical formulation, drug delivery system and method for increasing the rate at which an active agent permeates through the body surface of a patient, wherein the method involves administering the agent to a predetermined area of the patient's body surface in combination with an effective permeation enhancing amount of an enhancer composition comprised of a hydroxide-releasing agent and a lipophilic co-enhancer.

II. The Enhancer Composition

The enhancer composition is comprised of a hydroxide-releasing agent and a lipophilic co-enhancer, wherein the weight ratio of the hydroxide-releasing agent to the lipophilic co-enhancer is generally in the range of approximately 1:99 to approximately 99:1, preferably in the range of approximately 1:20 to approximately 20:1, and most preferably in the range of approximately 1:2 to approximately 2:1. The presence of the hydrophilic component, i.e., the hydroxide-releasing agent, ensures that the enhancer composition will be effective with hydrophilic drugs, while the presence of the lipophilic co-enhancer ensures that the enhancer composition will also be effective with hydrophobic (lipophilic) drugs. Further, the inventors herein have discovered that there is a synergistic effect in combining the two enhancer components, in that greater enhancement is observed with the combination of the hydroxide-releasing agent and the lipophilic co-enhancer than with the use of either enhancer component alone.

Preferably, although not necessarily, the enhancer composition has a pH in the range of approximately 8.0 to approximately 13.0, more preferably in the range of approximately 8.0 to 11.5, and optimally in the range of approximately 8.0 to approximately 11.5.

A. The Hydroxide-Releasing Agent

The "hydroxide-releasing agent" is a chemical compound that releases free hydroxide ions in the presence of an aqueous fluid. The aqueous fluid may be natural moisture at the skin surface, or a patch or composition that is used may contain added water, and/or be used in connection with an occlusive backing. Similarly, any liquid or semisolid formulation that is used is preferably aqueous or used in conjunction with an overlayer of an occlusive material.

Any hydroxide-releasing agent may be used provided that the compound releases free hydroxide ions in the presence of an aqueous fluid. Hydroxide-releasing agents useful as permeation enhancers are described in detail in co-pending U.S. patent application Ser. No. 09/738,410, filed Dec. 14, 2000, for "Hydroxide-Releasing Agents as Skin Permeation Enhancers" by Luo et al., assigned to Dermatrends, Inc. (San Diego, Calif.). As described in the aforementioned patent application, hydroxide-releasing agents that are suitable permeation enhancers include, but are not limited to, inorganic hydroxides, inorganic oxides, and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), ammonium phosphate (dibasic), and the like. Preferred hydroxide-releasing agents are metal hydroxides such as sodium hydroxide and potassium hydroxide.

It is important that the amount of hydroxide-releasing agent in any patch or formulation is optimized so as to increase the flux of the drug through the body surface while minimizing any possibility of skin damage. In general, this means that the pH at the body surface in contact with a formulation or drug delivery system of the invention (i.e., the interface between the body surface and the formulation or delivery system) should be in the range of approximately 8.0 to 13, preferably about 8.0 to 11.5, more preferably about 8.5 to 11.5. This will typically although not necessarily mean that the pH of a pharmaceutical formulation containing the enhancer composition and the active agent, or a drug composition contained within a delivery system, will be in the range of approximately 8.0 to 13, preferably about 8.0 to 11.5, more preferably about 8.5 to 11.5.

For inorganic hydroxides, the amount of hydroxide-releasing agent in a drug-containing pharmaceutical formulation for application to a patient's body surface will typically represent about 0.5 wt % to 4.0 wt %, preferably about 0.5 wt % to 3.0 wt %, more preferably about 0.75 wt % to 2.0 wt % and optimally about 1.0 wt %, of a topically applied formulation or of a drug reservoir of a drug delivery system, or "patch." The aforementioned amount applies to formulations and patches in which the active agent is (1) in nonionized, free base form, (2) a basic salt of an acidic drug, or (3) there are no additional species in the formulation or patch that could react with or be neutralized by the inorganic hydroxide.

More generally, however, the amount of the hydroxide-releasing agent in the formulation will be the total of (a) the amount required to neutralize any acidic species in the formulation plus (b) an amount equal to approximately 0.5 wt % to 4.0 wt %, preferably about 0.5 wt % to 3.0 wt %, more preferably about 0.75 wt % to 2.0 wt % and optimally about 1.0 wt %, of the formulation. Thus, when the active agent is an acid addition salt of a basic compound, the amount in (a) is the amount required to neutralize the acid addition salt and any other acidic species in the formulation. When the active agent is an acidic drug in the form of a free acid, the amount in (a) is the amount required to neutralize the acidic drug and any other acidic species in the formulation. As pointed out above, neither basic drugs in the form of a neutral, free base nor acidic drugs are affected by a hydroxide-releasing agent, and thus for these drugs, the amount in (a) is simply the amount necessary to neutralize inactive components that are acidic.

For other hydroxide-releasing agents such as inorganic oxides and metal salts of weak acids, the amount of hydroxide-releasing agent in the formulation or drug delivery system may be substantially higher, as high as 20 wt %, in some cases as high as 25 wt % or higher, but will generally be in the range of approximately 2 wt % to 20 wt %.

Still greater amounts of hydroxide-releasing agent may be used by controlling the rate and/or quantity of release of the hydroxide-releasing agent preferably during the drug delivery period itself.

However, for all hydroxide-releasing agents herein, the optimum amount of any particular agent will depend on the strength or weakness of the base, the molecular weight of the base, and other factors such as the number of ionizable sites in the drug administered and any other acidic species in the formulation or patch. One skilled in the art may readily determine the optimum amount for any particular agent by ensuring that a formulation or drug delivery system should in all cases be effective to provide a pH at the skin surface, during drug delivery, in the range of about 8.5 to 13, preferably in the range of about 8.5 to 11.5. This in turn ensures that the degree of enhancement is optimized while the possibility of damage to the body surface is eliminated or at least substantially minimized.

B. The Lipophilic Co-Enhancer

The lipophilic co-enhancer is selected from those enhancers typically referred to as "plasticizing" enhancers, i.e., enhancers that have a molecular weight in the range of about 150 to 1000, an aqueous solubility of less than about 1 wt %, preferably less than about 0.5 wt %, and most preferably less than about 0.2 wt %. The Hildebrand solubility parameter $\sigma$ of plasticizing enhancers is in the range of about 2.5 to about 10, preferably in the range of about 5 to about 10. As is known in the art, the Hildebrand solubility parameter measures the cohesive forces and sum of all intermolecular attractive forces related to the extent of mutual solubility of many chemical species. See, e.g., the CRC Handbook of Solubility Parameters and other Cohesion Parameters, CRC Press, Inc., Boca Raton, Fla. (1985). Relative hydrophilicity increases with the value of the Hildebrand solubility parameter. For example, the skin has a $\sigma$ value of 10, while water has a $\sigma$ value of 23.4. This in turn means enhancers with solubility parameters of <10 will intervene with the lipid components of the skin, but those with solubility parameters of >10 will selectively partition into the polar components of the skin. Such enhancers are distinguishable from "solvent-type" enhancers, which are lower molecular weight hydrophilic compounds having a higher solubility parameter $\sigma$ (as high as 18–20, or even higher).

The lipophilic co-enhancer preferably comprises a compound having the structure $(CH_3—L—X)_nR$, in which:

n is 1 or 2;

L is alkylene or alkenylene containing 1 to 3 double bonds and from about 6 to about 22 carbon atoms;

X is selected from the group consisting of —COO—, —$CH_2$O—, and —$CH_2$O—(CO)—; and R is selected from the group consisting of H, lower alkyl, and lower alkyl substituted with one or two hydroxyl groups, with the proviso that if R is H, X is necessarily —$CH_2$O—, wherein when n is 2, R contains at least two carbon atoms.

By "lower alkyl," applicants intend an alkyl group of 1 to 7 carbon atoms, typically 1 to 3 carbon atoms.

Preferred L moieties are alkylene linkers containing about 6 to about 22 carbon atoms, preferably about 8 to about 18 carbon atoms, more preferably about 8 to about 16 carbon atoms, and, for saturated aliphatic L moieties, most preferably 8 to 12 carbon atoms. It will be appreciated by those skilled in the art that since two additional carbon atoms are present within the entire compound (in "X" as well as in the methyl group bound to L), the most preferred compounds are actually: lower alkyl esters of $C_{10}$—$C_{18}$ fatty acids (X is —COO— and R is lower alkyl or lower alkyl substituted with one or two hydroxyl groups); lower alkyl ethers of $C_{10}$—$C_{18}$ fatty acids (X is —$CH_2$O— and R is lower alkyl or lower alkyl substituted with one or two hydroxyl groups); $C_{10}$—$C_{18}$ fatty alcohols (X is —$CH_2$O— and R is H); and esters of $C_{10}C_{18}$ fatty ethers and "lower" carboxylic acids (X is —$CH_2$O—(CO)— and R is lower alkyl or lower alkyl substituted with one or two hydroxyl groups); L may also be alkenylene, in which case 1 to 3, preferably 1 or 2, double bonds may be present, although one double bond (as in oleic acid) is typical.

Preferred lipophilic co-enhancers herein are fatty acid esters, particularly lower alkyl esters of saturated or unsaturated $C_{10}$–$C_{18}$ fatty acids, as noted above. Of the saturated $C_{10}$–$C_{18}$ fatty acids, most preferred are the $C_{10}$, $C_{12}$ and $C_{14}$ acids, i.e., capric acid, lauric acid, and myristic acid, respectively. Unsaturated $C_{10}$–$C_{18}$ fatty acids include oleic acid, palmitolcic acid, vaccenic acid, petroselenic acid, linoleic acid, linolenic acid, and linolaidic acid, with oleic acid being the most common and preferred herein. It will be appreciated from the definition of "n" that the fatty acid ester may comprise a single —X—L—$CH_3$ chain or two —X—L—$CH_3$ chains. In the latter case, the compound is a di-esterified dial or triol, with di-esterified $C_2$–$C_4$ alkane diols and triols preferred. For example, R may be selected from the group consisting of structures (II) through (V)

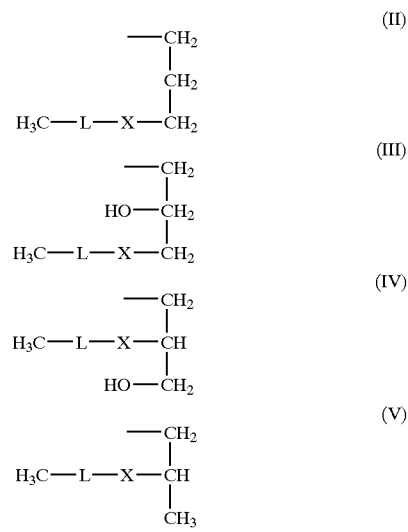

Examples of specific and most preferred fatty acid esters for use as lipophilic co-enhancers herein include, but are not limited to, methyl laurate, ethyl oleate, propylene glycol monolaurate, propylene glycerol dilaurate, glycerol monolaurate, glycerol monooleate, isopropyl n-decanoate, and octyldodecyl myristate, and the like.

The lipophilic co-enhancer may also be a fatty alcohol, in which case X is —$CH_2$O— and R is H, a fatty ether, in which case X is —$CH_2$O— and R is other than H, or an ester of a lower carboxylic acid with a fatty ether, in which case X is —$CH_2$O—(CO)— and R is other than H. Fatty alcohols include, for example, stearyl alcohol and oleyl alcohol, while fatty ethers include compounds wherein a diol or triol, preferably a $C_2$—$C_4$ alkane diol or triol, are substituted with one or two fatty ether substituents. Such fatty ethers include, for example, compounds wherein R is any one of structures (II) through (V), above.

C. Other Components of the Enhancer Composition

In addition to the hydroxide-releasing agent and the lipophilic co-enhancer, the enhancer composition may also include conventional additives such as opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. The enhancer composition may also contain one or more topical carriers, as described in Section IV, infra.

The enhancer composition may also contain irritation-mitigating additives to minimize or eliminate the possibility of skin irritation or skin damage resulting from the enhancer, the drug to be administered, or other components of the composition. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present enhancer compositions at a concentration effective to mitigate irritation or skin damage, typically representing not more than about 20 wt %, more typically not more than about 5 wt %, of the composition.

III. Pharmaceutical Formulations

In another embodiment, a pharmaceutical formulation is provided containing an effective permeation enhancing amount of the above-described enhancer composition, a therapeutically effective amount of a pharmacologically active agent, and a pharmaceutically acceptable carrier suitable for topical or transdermal drug administration. The formulation may be in any form suitable for application to the body surface, and may comprise, for example, a cream, lotion, solution, gel, ointment, paste or the like, and/or may be prepared so as to contain liposomes, micelles, and/or microspheres. It is preferred although not essential that water be present in order for the hydroxide-releasing agent to generate hydroxide ions and thus assist in enhancing the flux of the active agent through a patient's body surface. Thus, the formulation may be aqueous, i.e., contain water, or may be nonaqueous and optionally used in combination with an occlusive overlayer so that moisture evaporating from the body surface is maintained within the formulation or transdermal system during drug administration.

The amount of the hydroxide-releasing agent in the pharmaceutical formulation is preferably the total of (a) the amount required to neutralize any acidic species in the formulation plus (b) an amount equal to approximately 0.5 wt % to 4.0 wt % of the formulation. When the active agent is an acid addition salt of a basic compound, the amount in (a) is the amount required to neutralize the acid addition salt and any other acidic species in the formulation. When the active agent is an acidic drug in the form of a free acid, the amount in (a) is the amount required to neutralize the acidic drug and any other acidic species in the formulation. With basic drugs present in the formulation as a neutral, free base, and with basic salts of acidic drugs, the amount in (a) is simply the amount necessary to neutralize inactive components that are acidic, since such drugs are not, clearly, susceptible to neutralization with base. Like the enhancer composition, the pharmaceutical formulation preferably has a pH in the range of approximately 8.0 to approximately 13.0, more preferably in the range of approximately 8.0 to 11.5, and optimally in the range of approximately 8.0 to approximately 11.5.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington:. The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Pastes are semisolid dosage forms in which the active agent is suspended in a suitable base. Depending on the nature of the base, pastes are divided between fatty pastes or those made from a single-phase aqueous gel. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethyl-ammonium bromide, tetradecyltrimethylammonium bromide, tetradecyltrimethyl-ammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. For those drugs having an unusually low rate of permeation through the skin or mucosal tissue, it may be desirable to include a further permeation enhancer in the formulation, although in a preferred embodiment the hydroxide-releasing agent and lipophilic co-enhancer are administered without any other permeation enhancers. Any other enhancers should, like the hydroxide-releasing agent and the lipophilic co-enhancer, minimize the possibility of skin damage, irritation, and systemic toxicity. Examples of suitable additional enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethyl-ammonium bromide, benzalkonium chloride, Poloxamer (231, 182, 184), Tween (20, 40, 60, 80) and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}MSO$ may also be used, but are less preferred. As noted earlier herein, *Percutaneous Penetration Enhancers*, eds. Smith et al. (CRC Press, 1995) provides an excellent overview of the field and further information concerning possible secondary enhancers for use in conjunction with the present invention.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. Preferred formulations will typically contain on the order of about 0.5 wt % to 50 wt %, optimally about 10 wt % to 30 wt %, active agent.

IV. The Active Agent

The active agent administered may be any compound that is suitable for topical, transdermal or transmucosal delivery and induces a desired local or systemic effect. Such substances include the broad classes of compounds normally delivered through body surfaces and membranes, including skin. In general, this includes: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics;

peptide drugs; psychostimulants; sedatives; steroids; sympathomimetics; tranquilizers; and vasodilators including general coronary, peripheral and cerebral.

The active agent administered also may be one that is cosmetically or "cosmeceutically" effective rather than pharmacologically active. Such agents include, for example, compounds that can reduce the appearance of aging or photodamaged skin, e.g., alpha hydroxyacids, alpha ketoacids, polymeric hydroxyacids, moisturizers, collagen, marine extract, and antioxidants such as ascorbic acid (vitamin C), α-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (vitamin A), and/or cosmetically acceptable salts, esters, amides, or other derivatives thereof. A preferred tocopherol compound is α-tocopherol. Additional cosmetic agents include those that are capable of improving oxygen supply in skin tissue, as described, for example, in International Patent Publication Nos. WO 94/00098 and WO 94/00109. Sunscreens may also be included.

The active agent may be administered, if desired, in the form of a salt, ester, amide, prodrug, derivative, or the like, provided the salt, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

For those active agents that are chiral in nature and can thus be in enantiomerically pure form or in a racemic mixture, the drug may be incorporated into the present dosage units either as the racemate or in enantiomerically pure form.

The amount of active agent administered will depend on a number of factors and will vary from subject to subject and depend on the particular drug administered, the particular disorder or condition being treated, the severity of the symptoms, the subject's age, weight and general condition, and the judgment of the prescribing physician. Other factors, specific to transdermal drug delivery, include the solubility and permeability of the carrier and adhesive layer in a drug delivery device, if one is used, and the period of time for which such a device will be fixed to the skin or other body surface. The minimum amount of drug is determined by the requirement that sufficient quantities of drug must be present in a device or composition to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

Preferred classes of active agents are described in the following sections.

A. Pharmacologically Active Amines

The active agent may be a pharmacologically active nitrogen-containing base, for example, a primary amine, a secondary amine, or a tertiary amine, or it may be an aromatic or non-aromatic nitrogen-containing heterocycle, an azo compound, an imine, or a combination of any of the foregoing.

Examples of specific primary amines include, but are not limited to, amphetamine, norepinephrine, phenylpropanolamine (including any of the four isomers, individually or in combination, i.e., (+)-norephedrine, (−)-norephedrine, (+)-norpseudoephedrine, and (−)-norpseudoephedrine), and pyrithiamine.

Examples of secondary and tertiary amines include, but are not limited to, amiodarone, amitryptyline, azithromycin, benzphetamine, bromopheniramine, chlorambucil, chloroprocaine, chloroquine, chlorpheniramine, chlorothen, chlorpromazine, cinnarizine, clarthromycin, clomiphene, cyclobenzaprine, cyclopentolate, cyclophosphamide, dacarbazine, demeclocycline, dibucaine, dicyclomine, diethylproprion, diltiazem, dimenhydrinate, diphenhydramine, diphenylpyraline, disopyramide, doxepin, doxycycline, doxylamine, dypyridamine, ephedrine, epinephrine, ethylene diamine tetraacetic acid (EDTA), erythromycin, flurazepam, gentian violet, hydroxychloroquine, imipramine, isoproterenol, isothipendyl, levomethadyl, lidocaine, loxarine, mechlorethamine, melphalan, methadone, methafurylene, methapheniline, methapyrilene, methdilazine, methotimeperazine, methotrexate, metoclopramide, minocycline, naftifine, nicardipine, nicotine, nizatidine, orphenadrine, oxybutynin, oxytetracycline, phenindamine, pheniramine, phenoxybenzamine, phentolamine, phenylephrine, phenyltoloxamine, procainamide, procaine, promazine, promethazine, proparacaine, propoxycaine, propoxyphene, pyrilamine, ranitidine, scopolamine, tamoxifen, terbinafine, tetracaine, tetracycline, thonzylamine, tramadol, triflupromazine, trimeprazine, trimethylbenzamide, trimipramine, tripelennamine, troleandomycin, uracil mustard, verapamil and vonedrine.

Examples of non-aromatic heterocyclic amines include, but are not limited to, alprazolam, amoxapine, arecoline, astemizole, atropine, azithromycin, benazepril, benztropine, buprenorphine, buspirone, butorphanol, caffeine, capriomycin, ceftriaxone, chlorazepate, chlorcyclizine, chlordiazepoxide, chlorpromazine, chlorthiazide, ciprofloxacin, cladarabine, clemastine, clemizole, clindamycin, clofazamine, clonazepam, clonidine, clozapine, cocaine, codeine, cyclizine, cyproheptadine, dacarbzine, dactinomycin, desipramine, diazoxide, dihydroergotamine, diphenidol, diphenoxylate, dipyridamole, doxapram, ergotamine, estazolam, famciclovir, fentanyl, flavoxate, fludarabine, fluphenazine, flurazepam, fluvastatin, folic acid, ganciclovir, granisetron, guanethidine, halazepam, haloperidol, homatropine, hydrocodone, hydromorphone, hydroxyzine, hyoscyamine, imipramine, itraconazole, ketorolac, ketoconazole, levocarbustine, levorphan, lincomycin, lomefloxacin, loperamide, lorazepam, losartan, loxapine, mazindol, meclizine, meperidine, mepivacaine, mesoridazine, methdilazine, methenamine, methimazole, methotrimeperazine, methysergide, metronidazole, midazolam, minoxidil, mitomycin c, molindone, morphine, naftazone, nalbuphine, naldixic acid, nalmefene, naloxone, naltrexone, naphazoline, nedocromil, nicotine, norfloxacin, ofloxacin, ondansetron, oxazepam, oxycodone, oxymetazoline, oxymorphone, pemoline, pentazocine, pentostatin, pentoxyfylline, perphenazine, phentolamine, physostigmine, pilocarpine, pimozide, pramoxine, prazosin, prochlorperazine, promazine, promethazine, pyrrobutamine, quazepam, quinidine, quinine, rauwolfia alkaloids, riboflavin, rifabutin, risperidone, rocuronium, scopolamine, sufentanil, tacrine, temazepam, terazosin, terconazole, terfenadine, tetrahydrazoline, thioridazine, thiothixene, ticlodipine, timolol, tolazoline, tolazamide, tolmetin, trazodone, triazolam, triethylperazine, trifluopromazine, trihexylphenidyl, trimeprazine, trimipramine, tubocurarine, vecuronium, vidarabine, vinblastine, vincristine, vinorelbine and xylometazoline.

Examples of aromatic heterocyclic amines include, but are not limited to, acetazolamide, acyclovir, adenosine phosphate, allopurinal, alprazolam, amoxapine, amrinone, apraclonidine, azatadine, aztreonam, bisacodyl, bleomycin, brompheniramine, buspirone, butoconazole, carbinoxamine, cefamandole, cefazolin, cefixime, cefmetazole, cefonicid, cefoperazone, cefotaxime, cefotetan, cefpodoxime, ceftriaxone, cephapirin, chloroquine, chlorpheniramine, cimetidine, cladarabine, clotrimazole, cloxacillin, didanosine, dipyridamole, doxazosin, doxylamine, econazole, enoxacin, estazolam, ethionamide, famciclovir, famotidine, fluconazole, fludarabine, folic acid, ganciclovir, hydroxychloroquine, iodoquinol, isoniazid, isothipendyl, itraconazole, ketoconazole, lamotrigine, lansoprazole, lorcetadine, losartan, mebendazole, mercaptopurine, methafurylene, methapyriline, methotrexate, metronidazole, miconazole, midazolam, minoxidil, naldixic acid, niacin, nicotine, nifedipine, nizatidine, omeperazole, oxaprozin, oxiconazole, papaverine, pentostatin, phenazopyridine, pheniramine, pilocarpine, piroxicam, prazosin, primaquine, pyrazinamide, pyrilamine, pyrimethamine, pyrithiamine, pyridoxamine, quinidine, quinine, ribaverin, rifampin, sulfadiazine, sulfamethizole, sulfamethoxazole, sulfasalazine, sulfasoxazole, terazosin, thiabendazole, thiamine, thioguanine, thonzylamine, timolol, trazodone, triampterene, triazolam, trimethadione, trimethoprim, trimetrexate, triplenamine, tropicamide and vidarabine.

Examples of azo compounds are phenazopyridine and sulfasalazine, while examples of imines include cefixime, cimetidine, clofazimine, clonidine, dantrolene, famotidine, furazolidone, nitrofurantoin, nitrofurazone and oxiconazole.

Combinations of the aforementioned drugs and/or combinations of one or more of the aforementioned drugs with different type of active agent may also be delivered using the methodology of the present invention.

B. Nonsteroidal Antiinflammatory Agents (NSAIDS)

Suitable nonsteroidal antiinflammatory agents that may be used in the formulations of the present invention include, but are not limited to: propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; and combinations of any of the foregoing. Preferred NSAIDs are ibuprofen, diclofenac sodium, ketoprofen, ketorolac and piroxicam.

The NSAID or NSAIDs may be co-administered with one or more additional active agents, e.g.: antihistaminic agents such as diphenhydramine and chlorpheniramine (particularly diphenhydramine hydrochloride and chlorpheniramine maleate); corticosteroids, including lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, and methylprednisolone, as well as higher potency corticosteroids such as clobetasol propionate, betamethasone benzoate, betamethasone diproprionate, diflorasone diacetate, fluocinonide, mometasone furoate, triamcinolone acetonide, and the like; local anesthetic agents such as phenol, benzocaine, lidocaine, prilocaine and dibucaine; topical analgesics such as glycol salicylate, methyl salicylate, 1-menthol, d,1-camphor and capsaicin; and antibiotics. Preferred additional agents are antibiotic agents, discussed in Section F, infra.

The aforementioned compounds may be administered transdermally using the compositions, system and method of the invention to treat any patient with an NSAID-responsive condition or disorder. Typically, NSAMDs are employed as anti-inflammatory and/or analgesic agents, and accordingly may be used to treat individuals suffering from rheumatic or arthritic disorders, including, for example: rheumatoid arthritis (RA), degenerative joint disease (also known as DJD and "osteoarthritis"); juvenile rheumatoid arthritis (JRA); psoriatic arthritis; gouty arthritis; ankylosing spondylitis; and lupus erythematoses such as systemic lupus erythematosus and discoid lupus erythematosus.

Other potential uses of NSAIDs include, but are not limited to, treating fever (via the anti-pyretic property of NSAIDs) or myocardial infarction (MI), transient ischemic attacks, and acute superficial thrombophlebitis (via inhibition of platelet aggregation). Further non-limiting uses for NSAIDs include either single or adjuvant therapy for ankylosing spondylitis, bursitis, cancer-related pain, dysmenorrhea, gout, headaches, muscular pain, tendonitis, and pain associated with medical procedures such as dental, gynecological, oral, orthopedic, post-partum and urological procedures.

The amount of active agent administered will depend on a number of factors and will vary from subject to subject, as noted above. Generally, however, and by way of example, a daily dosage of ketorolac using the present formulations and systems will be in the range of approximately 10 mg to 40 mg, a daily dosage of piroxicam using the present formulations and systems will be in the range of approximately 10 mg to 40 mg, and a daily dosage of ibuprofen using the present formulations and systems will be in the range of approximately 200 mg/day to 1600 mg/day.

C. Steroids

1. Estrogens and Progestins

Suitable estrogens that may be administered using the compositions and drug delivery systems of the invention include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. 17β-Estradiol, ethinylestradiol and mestranol are particularly preferred synthetic estrogenic agents for use in conjunction with the present invention.

Suitable progestins that can be delivered using the compositions and systems of the invention include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethyl-progesterone, hydroxymethyl-progesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, medroxyprogesterone, norethindrone, norethynodrel, d,1-norgestrel and 1-norgestrel are particularly preferred progestins.

It is generally desirable to co-administer a progestin along with an estrogen in female HRT so that the estrogen is not "unopposed." As is well known, estrogen-based therapies are known to increase the risk of endometrial hyperplasia and cancer, as well as the risk of breast cancer, in treated individuals. Co-administration of estrogenic agents with a progestin has been found to decrease the aforementioned risks. Preferred such combinations include, without limitation: 17β-estradiol and medroxyprogesterone acetate; 17β-estradiol and norethindrone; 17β-estradiol and norethynodrel; ethinyl estradiol and d,1-norgestrel; ethinyl estradiol and 1-norgestrel; and megestrol and medroxyprogesterone acetate.

For female HRT, it may be desirable to co-administer a small amount of an androgenic agent along with the progestin and the estrogen, in order to reproduce the complete hormone profile of the premenopausal woman, since low levels of certain androgens are present in premenopausal women.

Any of the aforementioned steroid drugs may be naturally occurring steroids, synthetic steroids, or derivatives thereof.

As alluded to above, administration of a combination of steroidal active agents is useful in a variety of contexts, as will be readily appreciated by those skilled in the art. For example, the transdermal administration of a progestin with an estrogen may be used in female hormone replacement therapy, so that the symptoms or conditions resulting from altered hormone levels is mitigated or substantially prevented. The present compositions and drug delivery systems are in addition useful to administer progestins and estrogens to treat other conditions and disorders that are responsive to transdermal administration of the combination of active agents. For example, the aforementioned combination is useful to treat the symptoms of premenstrual stress and for female contraception, as noted above. For female hormone replacement therapy, the woman undergoing treatment will generally be of childbearing age or older, in whom ovarian estrogen, progesterone and androgen production has been interrupted either because of natural menopause, surgical procedures, radiation, chemical ovarian ablation or extirpation, or premature ovarian failure. For hormone replacement therapy, and for the other indications described herein including female contraception, the compositions or drug delivery systems are preferably used consecutively so that administration of the active agents is substantially continuous. Transdermal drug administration according to the invention provides highly effective female hormone replacement therapy. That is, the incidence and severity of hot flashes and night sweats are reduced, postmenopausal loss of calcium from bone is minimized, the risk of death from ischemic heart disease is reduced, and the vascularity and health of the Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties. However, preferred transdermal compositions and systems for hormone replacement therapy are capable of delivering about 0.5 to 10.0 mg progestin, e.g., norethindrone, norethindrone acetate or the like, and about 10 to 200 μg estrogen, e.g., 17β-estradiol, ethinyl estradiol, mestranol or the like, over a period of about 24 hours. However, it will be appreciated by those skilled in the art that the desired dose of each individual active agent will depend on the specific active agent as well as on other factors; the minimum effective dose of each active agent is of course preferred.

2. Androgenic Drugs

Suitable androgenic agents that may be administered using the compositions, system and method of the invention include, but are not limited to: the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, are particularly preferred androgenic agents for use in conjunction with the present invention. The aforementioned testosterone esters are commercially available or may be readily prepared using techniques known to those skilled in the art or described in the pertinent literature.

The aforementioned androgenic agents are selected from the group consisting of naturally occurring androgens, synthetic androgens, and derivatives thereof. The active agents may be incorporated into the present dosage units and thus administered in the form of a pharmaceutically acceptable derivative, analog, ester, salt, or amide, or the agents may be modified by appending one or more appropriate functionalities to enhance selected biological properties such as penetration through mucosal tissue. In general, with regard to androgenic agents, esters are preferred relative to salts or other derivatives. Preparation of esters, as noted in the preceding section, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters can be reconverted to the free acids, if desired, by using conventional hydrogenolysis or hydrolysis procedures.

Androgenic drugs such as testosterone (17β-hydroxyandrost-4-en-3-one) are required for sperm production and promote general growth of body tissues. The primary clinical use of androgens is to replace or augment androgen secretion in hypogonadal men. Androgens may also be used to treat certain gynecologic disorders, such as to reduce breast engorgement during the postpartum period. Androgens may also be used to reduce protein loss after trauma, surgery, or prolonged immobilization, or in the treatment of anemia and hereditary angioedema. Androgens may additionally be used in the treatment of male osteoporosis or as metabolic growth stimulators in prepubertal boys.

Testosterone and its derivatives are compounds that are therapeutically effective at fairly low doses, generally in the range of approximately 5 to 10 mg/day.

D. Peptidyl Drugs

Peptidyl drugs that can be administered according to the invention include any pharmacologically active peptides, polypeptides or proteins. Once chosen, the peptidyl drug must be prepared or obtained from commercial suppliers for incorporation into a composition or delivery system. The peptidyl drug may be prepared using standard synthetic techniques, recombinant technology or extraction from natural sources.

Synthetic production of peptides, polypeptides and proteins generally employs techniques of standard solid phase peptide synthesis well known in the art. In such a method, the synthesis is sequentially carried out by incorporating the desired amino acid residues one at a time onto a growing peptide chain according to the general principles of solid phase synthesis as described, for example, by Merrifield (1963) *J. Amer. Chem. Soc.* 85:2149-2154. Common to chemical syntheses of peptides, polypeptides and proteins is the protection of reactive side chain groups of the various amino acid moieties with suitable protecting groups that will prevent a chemical reaction from occurring at that site until the protecting group is ultimately removed. It is also well known to protect the α-amino group on an amino acid while that entity reacts at the carboxyl group, followed by the selective removal of the α-amino protecting group to allow a subsequent reaction to take place at that site. Examples of suitable α-amino and side chain protecting groups are well known in the art.

Alternatively, the peptide, polypeptide or protein may be prepared by employing recombinant technology via techniques well known in the art. That is, conventional recombinant techniques may be used, which, as will be appreciated by those skilled in the art, involves constructing DNA encoding the desired amino acid sequence, cloning the DNA into an expression vector, transforming a host cell, e.g., a bacterial, yeast, or mammalian cell, and expressing the DNA to produce the desired peptide, polypeptide or protein.

Additionally, peptides, polypeptides or proteins can be obtained from natural sources such as a human or other animal, and may be extracted from either a living organism or from a cadaver. The material is separated and purified prior to incorporation into a drug delivery system or dosage form. Techniques of separation and purification are well known in the art and include, for example, centrifugation and Although any peptidyl drug may be incorporated into the delivery systems of the present invention, the drug is generally selected from coagulation modulators, cytokines, endorphins, kinins, hormones, LHRH (luteinizing hormone-releasing hormone) analogs and other peptidyl drugs that provide a desired pharmacological activity. Of course, the categories provided are not intended to be limiting and simply serve as a means for organization. As will be appreciated, a peptidyl drug may fall into more than one category.

Coagulation modulators include, for example, $\alpha_1$-antitrypsin, $\alpha_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, thrombomodulin and combinations thereof. When applicable, both the "active" and "inactive" versions of these proteins are included.

Preferred cytokines include, without limitation, colony stimulating factor 4, heparin binding neurotrophic factor (HBNF), interferon-α, interferon α-2a, interferon α-2b, interferon α-n3, interferon-β, interferon-γ, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), thymopoietin and combinations thereof.

Preferred endorphins include, but are not limited to, dermorphin, dynorphin, α-endorphin, β-endorphin, γ-endorphin, σ-endorphin [Leu$^5$]enkephalin, [Met$^5$] enkephalin, substance P, and combinations thereof.

Preferred peptidyl hormones include activin, amylin, angiotensin, atrial natriuretic peptide (ANP), calcitonin (derived from chicken, eel, human, pig, rat, salmon, etc.), calcitonin gene-related peptide, calcitonin N-terminal flanking peptide, cholecystokinin (CCK), ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, ghrelin, glucogon, gonadotropin-releasing factor (GnRF or GNRH), growth hormone releasing factor (GRF, GRH), human chorionic gonadotropin (hCH), inhibin A, inhibin B, insulin (derived from beef, human, pig, etc.), leptin, lipotropin (LPH), luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, triiodothyronine, vasoactive intestinal peptide (VIP), vasopressin (antidiuretic hormone, ADH) and combinations thereof.

Particularly preferred analogues of LHRH include buserelin, deslorelin, fertirelin, goserelin, histrelin, leupolide (leuprorelin), lutrelin, nafarelin, tryptorelin and combinations thereof.

Particularly preferred kinins include bradykinin, potentiator B, bradykinin potentiator C, kallidin and combinations thereof.

Still other peptidyl drugs that provide a desired pharmacological activity can be incorporated into the delivery systems of the invention. Examples include abarelix, adenosine deaminase, anakinra, ancestim, alteplase, alglucerase, asparaginase, bivalirudin, bleomycin, bombesin, desmopressin acetate, des-Q14-ghrelin, dornase-α, enterostatin, erythropoietin, exendin-4, fibroblast growth factor-2, filgrastim, β-glucocerebrosidase, gonadorelin, hyaluronidase, insulinotropin, lepirudin, magainin I, magainin II, nerve growth factor, pentigetide, thrombopoietin, thymosin α-1, thymidin kinase (TK), tissue plasminogen activator, tryptophan hydroxylase, urokinase, urotensin II and combinations thereof.

E. Locally Administered Active Agents

Preferred agents for local, topical administration are within the broad classes of compounds known to be topically administrable, including, but not limited to, topical antibiotics and other anti-acne agents, anti-fungal agents, anti-psoriatic agents, antipruritic agents, antihistamines, antineoplastic agents, local anesthetics, anti-inflammatory agents and the like. Suitable topical antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin itself (6,8-dideoxy-6-[[( 1-methyl-4-propyl-2-pyrrolidinyl)-carbonyl] amino]-1-thio-L-threo-α-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]-amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof Exemplary antibiotics of the tetracycline family include tetracycline itself 4-(dimethylamino)- 1,4,4α,5,5α6,11,12α-octahydro-3,6,12,12α-pentahydroxy-6-m ethyl-1,11-dioxo-2-naphthacene-carboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Topical anti-acne agents include keratolytics such as salicylic acid, retinoic acid ("Retin-A"), and organic peroxides, while topical antifungal agents include amphotericin B, benzoic acid, butoconazole, caprylic acid, econazole, fluconazole, itraconazole, ketoconazole, miconazole, nystatin, salicylic acid, and terconazole, and topical antipsoriatic agents include anthralin, azathioprine, calcipotriene, calcitriol, coichicine, cyclosporine, retinoids, and vitamin A. The active agent may also be a topical corticosteroid, and may be one of the lower potency corticosteroids such as hydrocortisone, hydrocortisone-2-monoesters (e.g., hydrocortisone-21-acetate, hydrocortisone-21-butyrate, hydrocortisone-2-propionate, hydrocortisone-2-valerate, etc.), hydrocortisone-17,21-diesters (e.g., hydrocortisone- 17,21-diacetate, hydrocortisone- 17-acetate-21-butyrate, hydrocortisone- 17,21-dibutyrate, etc.), alclometasone, dexamethasone, flumethasone, prednisolone, or methylprednisolone, or may be a higher potency corticosteroid such as clobetasol propionate, betametbasone benzoatc, betamethasone diproprionate, diflorasone diacetate, fluocinonide, niometasone furoate, triamcinolone acetonide, or the like.

F. Other Active Agents and Analogs

Still other examples of active agents with which the novel enhancer compositions may be advantageously employed include, but are not limited to, the following:

analgesic and anesthetic agents—hydrocodone, hydromorphone, levorphanol, oxycodone, oxymorphone, codeine, morphine, alfentanil, fentanyl, meperidine, sufentanil, buprenorphine, and nicomorphine;

antidepressant drugs—selective serotonin reuptake inhibitors such as sertraline, paroxetine, fluoxetine, fluvoxamine, citalopram, venlafaxine and nefazodone; tricyclic anti-depressants such as amitriptyline, doxepin, nortriptyline, imipramine, trimipramine, amoxapine, desipramine, protriptyline, clomipramine, mirtazapine and maprotiline; other anti-depressants such as trazodone, buspirone and bupropion;

attention deficit disorder and attention deficit hyperactivity disorder drugs—methylphenidate and pemoline;

cardiovascular preparations—angiotensin converting enzyme (ACE) inhibitors such as enalapril, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1S-pentyl) amino-2,3,4,5-tetrahydro-2-oxo-3S-1H-1-benzazepine-1-acetic acid or 3-(1-ethoxycarbonyl-3-phenyl-(1S)-propylamino)-2,3,4,5-tetrahydro-2-oxo-(3S)-benzazepine-1-acetic acid monohydrochloride; diuretics; pre- and afterload reducers; cardiac glycosides such as digoxin and digitoxin; inotropes such as amrinone and milrinone; calcium channel blockers such as verapamil, nifedipine, nicardipene, felodipine, isradipine, nimodipine, bepridil, amlodipine and diltiazem; beta-blockers such as metoprolol; pindolol, propafenone, propranolol, esmolol, sotalol and acebutolol; antiarrhythmics such as moricizine, ibutilide, procainamide, quinidine, disopyramide, lidocaine, phenytoin, tocainide, mexiletine, flecainide, encainide, bretylium and amiodarone; cardioprotective agents such as dexrazoxane and leucovorin; vasodilators such as nitroglycerin; cholinergic agents such as arecoline;

CNS agents—bromocriptine, ±trans-1,3,4,4α,5,10β-hexahydro-4-propyl-2H-1-benzopyrano-3,4-bipyridine-9-ol monohydrochloride;

muscle relaxants—baclofen;

nicotine;

narcotic antagonists—naloxone, particularly naloxone hydrochloride;

peripheral vascular dilators—cyclandelate, isoxsuprine and papaverine;

ophthalmic drugs—physostigmine sulfate;

respiratory drugs—such as albuterol, formoterol, nikethamide, theophylline, terbutaline, oxytriphylline, aminophylline and other xanthine derivatives; and topoimerase inhibitors—topotecan and irinotecan.

Genetic material may also be delivered using the methods, formulations and transdermal systems of the invention, e.g., a nucleic acid, RNA, DNA, recombinant RNA, recombinant DNA, antisense RNA, antisense DNA, a ribooligonucleotide, a deooxyriboonucleotide, an anti sense ribooligonucleotide, or an antisense deoxyriboooligonucleotide.

Particularly preferred systemically active agents that can be administered transdermally in conjunction with the present invention are as follows: buprenorphine, fentanyl, sufentanil, terbutaline, formoterol, albuterol, theophylline, estradiol, progesterone, scopolamine, enalapril, 1-carboxymethyl-3-1-carboxy-3-phenyl-(1S)-propylamino-2,3,4,5-tetrahydro-1H-(3S)1 3-(5-amino-1-carboxy-1S-pentyl)amino-2,3,4,5-tetrahydro-2-oxo-3S-1H-1-benzazepine 1-acetic acid, 3-(1-ethoxycarbonyl-3-phenyl-(1S)-propylamino)-2,3,4,5-tetrahydro-2-oxo-(3S)-benzazepion-1-acid monohydrochloride; nitroglycerin, triprolidine, tripelenamine, diphenhydramine, physostigmine, arecoline, and nicotine. Uncharged, nonionizable active agents are preferred, as are acid addition salts of basic drugs. Of the latter group, the hydrochloride salt is most preferred.

V. Drug Delivery Systems:

An alternative and preferred method involves the use of a drug delivery system, e.g., a topical or transdermal "patch," wherein the active agent is contained within a laminated structure that is to be affixed to the skin. In such a structure, the drug and enhancer composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element that serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent and/or the lipophilic co-enhancer, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

It will also be appreciated by those skilled in the art that the enhancer composition and the drug(s) may be contained in separate patches each applied to the patient's body surface. Alternatively, the drug delivery device may comprise two or more patch segments each containing different components (e.g., one may contain the drug and the other may contain the enhancer composition) that are assembled immediately prior to use.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of drug to be delivered and the flux of the drug through the body surface. Larger patches will necessary to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The enhancer composition will generally be incorporated into the device during patch manufacture rather than subsequent to preparation of the device. Thus, for acid addition salts of basic drugs (e.g., hydrochloride salts of amine drugs, such as phenylpropanolamine hydrochloride), the hydroxide-releasing agent present in the enhancer composition will neutralize the drug during manufacture of the drug delivery system, resulting in a final drug delivery system in which the drug is present in nonionized, neutral form along with an excess of hydroxide-releasing agent. For nonionized acidic drugs, the hydroxide-releasing agent will neutralize such drugs by converting them to the ionized drug in salt form.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such adhesive overlayer, the delivery system remains in place for the required period of time.

Other types and configurations of transdermal drug delivery systems may also be used in conjunction with the present invention, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the topically applied formulations of the invention, the composition that contains the drug and permeation enhancer composition within the drug reservoir(s) of these laminated system may contain a number of additional components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components that may be present include preservatives, stabilizers, surfactants, and the like.

VI. Method of Use

The method of delivery of the active agent may vary, but necessarily involves application of a drug and the enhancer composition of the invention to a predetermined area of the skin or other tissue for a period of time sufficient to provide the desired local or systemic effect. The method may involve pretreatment of the body surface with the enhancer composition, followed by application of a pharmaceutical formulation or drug delivery device. More commonly, the method of drug delivery will involve direct application of the pharmaceutical formulation as an ointment, gel, cream, or the like, or may involve use of a drug delivery device. The delivery device is generally maintained in place on the body surface throughout the drug delivery period established for a particular active agent.

The invention accordingly provides a novel and highly effective means for increasing the flux of an active agent through the body surface (skin or mucosal tissue) of a human or animal. The enhancer compositions discussed herein may be used as permeation enhancers with a wide variety of drugs and drug types, including both hydrophilic and hydrophobic drugs. The increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. Furthermore, the practice of the present invention will employ, unless otherwise indicated, conventional techniques of drug formulation, particularly topical and transdermal drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

All patents, patent applications, patent publications, journal articles and other references cited herein are incorporated by reference in their entireties.

The following example is put forth so as to provide those of ordinary skill in the art with a complete disclosure and description of how to make and use the compounds of the invention, and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE

An in-vitro skin permeation study was conducted using four testosterone transdermal systems. The formulations used to prepare these systems are listed in Table 1, which include weight and weight percent of each ingredient in the formulations. Formulation Test-P 178 contained no oleic acid and no NaOH. Formulation Test-P179 contained both NaOH and oleic acid. Formulation Test-P180 contains NaOH without oleic acid. Formulation Test-181 contained oleic acid without NaOH.

Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of $11/16$ inch.

The in-vitro permeation of testosterone through human cadaver skin from these discs was performed using Franz-type diffusion cells with a diffusion area of 1 $cm^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The receiver solution was completely withdrawn and replaced with fresh solution at each time point. The samples taken were analyzed by an HPLC for the concentration of testosterone in the receiver solution. The cumulative amount of testosterone across human cadaver skin was calculated using the measured testosterone concentrations in the receiver solutions, which were shown in Table 2 and FIG. 1.

TABLE 1

Weight and Weight Percent of Each Ingredient Based on Total Solution Weight for Four Testosterone Transdermal Systems

| Component | Test-P178 | Test-P179 | Test-P180 | Test-P181 |
|---|---|---|---|---|
| Polymer | 0.25 g | 0.25 g | 0.25 g | 0.25 g |
| THF | 1.25 g | 1.25 g | 1.25 g | 1.25 g |
| Benzyl alcohol | 0.7 g | 0.7 g | 0.7 g | 0.7 g |
| Glycerin | 0.7 g | 0.7 g | 0.7 g | 0.7 g |
| Oleic acid | 0 | 0.2 g | 0 | 0.2 g |
| Protalan | 0.15 g | 0.15 g | 0.15 g | 0.15 g |
| Vitamin E | 0.3 g | 0.3 g | 0.3 g | 0.3 g |
| Urea | 0.2 g | 0.2 g | 0.2 g | 0.2 g |
| NaOH | 0 | 0.09 g | 0.09 g | 0 |
| Water | 0 | 0.09 g | 0.09 g | 0 |
| Testosterone | 0.5 g | 0.5 g | 0.5 g | 0.5 g |

TABLE 2

Cumulative Amount of testosterone across human cadaver skin for Testosterone Transdermal Systems (mg/cm$^2$)

| Measurement time | Test-P178 | Test-P179 | Test-P180 | Test-P181 |
|---|---|---|---|---|
| 4.75 hours | 0.005 | 0.027 | 0.036 | 0.006 |
| 15.5 hours | 0.022 | 0.189 | 0.167 | 0.027 |
| 19.5 hours | 0.033 | 0.258 | 0.209 | 0.038 |
| 24 hours | 0.044 | 0.346 | 0.254 | 0.051 |

The cumulative amount of testosterone across human cadaver skin at 24 hours for Test-P179 (contained dual enhancers, NaOH and oleic acid) was 0.346 mg/cm$^2$, which was higher than that for Test-P180 (0.254 mg/cm$^2$, containing NaOH without oleic acid) or that for Test-P181 (0.051 mg/cm$^2$, containing oleic acid without NaOH). The cumulative amount of testosterone across human cadaver skin at 24 hours for Test-P178 containing no NaOH and no oleic acid is the lowest among these four formulations, which is 0.044 mg/cm$^2$. The results are illustrated in graph form in FIG. 1.

The method may be repeated using other pharmacologically active agents (e.g., other steroids, NSAIDs, peptidyl drugs, etc.; see Section IV), permeation enhancing bases (e.g., other inorganic hydroxides, inorganic oxides, and alkali metal or alkaline earth metal salts of weak acids; see Section IIA), and lipophilic co-enhancers (e.g., methyl laurate, ethyl oleate, propylene glycol monolaurate, propylene glycerol dilaurate, glycerol monolaurate, glycerol monooleate, isopropyl n-decanoate, and octyldodecyl myristate; see Section IIB) as described herein, and substantially the same results will be obtained.

We claim:

1. A method for enhancing the flux of a drug through a body surface, comprising administering the drug to a localized region of a human patient's body surface in combination with an effective permeation enhancing amount of permeation enhancer composition comprised of a hydroxide-releasing agent and a lipophilic co-enhancer, said lipophilic co-enhancer being selected from the group consisting of:

(i) a compound having a molecular weight in the range of about 150 to 1000 and an aqueous solubility of less than about 1 wt %, and the structure (CH$_3$—L—X)$_n$R, wherein: n is 1 or 2; L is alkylene or alkenylene containing 1 to 3 double bonds, and from about 6 to about 22 carbon atoms; X is selected from the group consisting of—COO—, —CH2O—, and —CH$_2$O—(CO)—; and R is selected from the group consisting of H, lower alkyl, and lower alkyl substituted with one or two hydroxyl groups, with the proviso that if R is H, X is necessarily —CH$_2$O—, and wherein when n is 2, R contains at least two carbon atoms;

(ii) a lower alkyl ester of a C$_{10}$–C$_{18}$ fatty acid; and (iii) an esterified polyol selected from the group consisting of propylene glycol mono- or di-substituted with a C$_{10}$–C$_{18}$ fatty acid and glycerol mono- or di-substituted with a C$_{10}$–C$_{18}$ fatty acid;

wherein the composition is effective to provide a pH in the range of approximately 8.0 to 13.0 at the localized region of the body surface, and the amount of hydroxide-releasing agent in the composition is the total of (a) the amount required to neutralize any acidic species in the composition plus (b) an amount equal to approximately 0.5 wt % to 25 wt % of the composition.

2. The method of claim 1, wherein the pH is in the range of approximately 8.0 to 11.5.

3. The method of claim 1, wherein the body surface is skin.

4. The method of claim 1, wherein the body surface is mucosal tissue.

5. The method of claim 1, wherein the composition is aqueous.

6. The method of claim 5, wherein the composition is selected from the group consisting of a cream, a gel, a lotion, and a paste.

7. The method of claim 1, wherein the composition is nonaqueous.

8. The method of claim 7, wherein the composition is an ointment.

9. The method of claim 1, wherein the hydroxide-releasing agent releases free hydroxide ions in the presence of an aqueous fluid.

10. The method of claim 1, wherein the hydroxide-releasing agent is selected from the group consisting of inorganic hydroxides, inorganic oxides, metal salts of weak acids, and mixtures thereof.

11. The method of claim 10, wherein the hydroxide-releasing agent is an inorganic hydroxide.

12. The method of claim 11, wherein the inorganic hydroxide is selected from the group consisting of ammonium hydroxide, alkali metal hydroxides, alkaline earth metal hydroxides, and mixtures thereof.

13. The method of claim 12, wherein the inorganic hydroxide is selected from the group consisting of ammonium hydroxide, sodium hydroxide, calcium hydroxide, potassium hydroxide, magnesium hydroxide, and mixtures thereof.

14. The method of claim 13, wherein the inorganic hydroxide is sodium hydroxide.

15. The method of claim 13, wherein the inorganic hydroxide is potassium hydroxide.

16. The method of claim 11, wherein the amount of inorganic hydroxide in the composition is the total of (a) the amount required to neutralize any acidic species in the composition plus (b) an amount equal to approximately 0.5 wt % to 4.0 wt % of the composition.

17. The method of claim 16, wherein the amount of inorganic hydroxide in the composition is the total of (a) the amount required to neutralize any acidic species in the composition plus (b) an amount equal to approximately 0.5 wt. % to 3.0 wt. % of the composition.

18. The method of claim 17, wherein the amount of inorganic hydroxide in the composition is the total of (a) the amount required to neutralize any acidic species in the composition plus (b) an amount equal to approximately 0.75 wt. % to 2.0 wt. % of the composition.

19. The method of claim 10, wherein the hydroxide-releasing agent is an inorganic oxide.

20. The method of claim 19, wherein the inorganic oxide is selected from the group consisting of magnesium oxide, calcium oxide, and mixtures thereof.

21. The method of claim 19, wherein the composition contains up to approximately 20 wt. % of the hydroxide-releasing agent.

22. The method of claim 10, wherein the hydroxide-releasing agent is a metal salt of a weak acid.

23. The method of claim 22, wherein the hydroxide-releasing agent is selected from the group consisting of sodium acetate, sodium carbonate, tribasic sodium phosphate, dibasic sodium phosphate, sodium borate, potassium carbonate, potassium acetate, dibasic potassium phosphate, tribasic potassium phosphate, sodium metaborate, and mixtures thereof.

24. The method of claim 22, wherein the composition contains up to approximately 20 wt. % of the hydroxide-releasing agent.

25. The method of claim 1, wherein L is alkylene.

26. The method of claim 25, wherein L has a total of from about 8 to about 12 carbon atoms.

27. The method of claim 1, wherein L is alkenylene.

28. The method of claim 27, wherein L has a total of from about 8 to about 18 carbon atoms.

29. The method of claim 28, wherein L has a total of from about 8 to about 16 carbon atoms.

30. The method of claim 1, wherein X is —COO—.

31. The method of claim 30, wherein n is 1 and R is lower alkyl.

32. The method of claim 30, wherein n is 1 and R is lower alkyl substituted with one or two hydroxyl groups.

33. The method of claim 30, wherein n is 2 and R is lower alkyl substituted with one or two hydroxyl groups.

34. The method of claim 30, wherein R is selected from the group consisting of

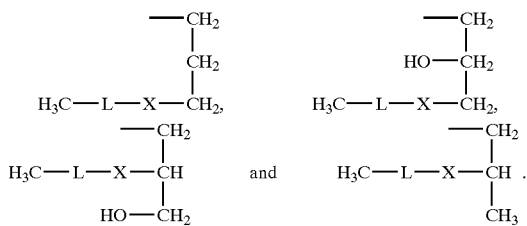

35. The method of claim 1, wherein X is —CH$_2$O— and R is lower alkyl or lower alkyl substituted with one or two hydroxyl groups.

36. The method of claim 1, wherein X is —CH$_2$O— and R is H.

37. The method of claim 1, wherein X is —CH$_2$O—(CO)— and R is lower alkyl.

38. The method of claim 1, wherein X is —CH$_2$O—(CO)— and R is lower alkyl substituted with one or two hydroxyl groups.

39. The method of claim 1, wherein the weight ratio of the hydroxide-releasing agent to the lipophilic co-enhancer is in the range of approximately 1:99 to approximately 99:1.

40. The method of claim 39, wherein the weight ratio of the hydroxide-releasing agent to the lipophilic co-enhancer is in the range of approximately 1:20 to approximately 20:1.

41. The method of claim 40, wherein the weight ratio of the hydroxide-releasing agent to the lipophilic co-enhancer is in the range of approximately 1:2 to approximately 2:1.

42. The method of claim 1, wherein the drug and the permeation enhancer composition are administered by applying a drug delivery device to the localized region of the patient's body surface thereby forming a body surface-delivery device interface, the device comprising the drug and the permeation enhancer composition, and having an outer backing layer that serves as the outer surface of the device during use.

43. The method of claim 1, wherein the drug is selected from the group consisting of: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder and attention deficit hyperactivity disorder drugs; calcium channel blockers; beta-blockers; antiarrhythmic agents; central nervous system stimulants; decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents; ophthalmic drugs; parasympatholytics; peptide drugs; psychostimulants; sedatives; steroids; sympathomimetics; tranquilizers; vasodilators; and combinations thereof.

44. The method of claim 1, wherein the drug is an acid addition salt of a basic compound, and the amount in (a) is the amount required to neutralize the acid addition salt and any other acidic species in the composition.

45. The method of claim 1, wherein the drug is an acidic drug in the form of a free acid, and the amount in (a) is the amount required to neutralize the acidic drug and any other acidic species in the composition.

46. The method of claim 1, wherein the drug is a basic drug is the form of a free base.

47. The method of claim 1, wherein the drug is a basic addition salt of an acidic compound.

48. The method of claim 1, wherein the drug is nonionizable.

* * * * *